(12) United States Patent  
Esposito et al.

(10) Patent No.: US 8,047,850 B2
(45) Date of Patent: Nov. 1, 2011

(54) TRAINING TOURNIQUET AND METHOD OF USE

(75) Inventors: Mark Esposito, Golden, CO (US); Jonathan Bennett, Fort Mill, SC (US)

(73) Assignee: Phil Durango, LLC, Golden, CO (US)

( * ) Notice: Subject to any disclaimer, the term of this patent is extended or adjusted under 35 U.S.C. 154(b) by 796 days.

(21) Appl. No.: 12/163,796

(22) Filed: Jun. 27, 2008

(65) Prior Publication Data

US 2009/0005804 A1    Jan. 1, 2009

Related U.S. Application Data

(60) Provisional application No. 60/947,337, filed on Jun. 29, 2007.

(51) Int. Cl.
*G09B 23/28* (2006.01)
(52) U.S. Cl. .......................... 434/262; 434/275
(58) Field of Classification Search .............. 434/262, 434/265, 267, 268, 272, 275; 606/203; 446/295
See application file for complete search history.

(56) References Cited

U.S. PATENT DOCUMENTS

| | | |
|---|---|---|
| 1,500,629 A | 7/1924 | Levy |
| 1,569,131 A | 1/1926 | Nord |
| 1,606,841 A | 11/1926 | Newton |
| 1,698,813 A | 1/1929 | Gouirand |
| 2,084,412 A | 6/1937 | Schaefer |
| 2,387,428 A | 10/1945 | Brothers |
| 2,480,430 A | 8/1949 | Nugent |
| 2,553,390 A | 5/1951 | Streyckmans |
| 2,661,888 A | 12/1953 | Sidlinger |
| 3,095,873 A | 7/1963 | Edmunds, Jr. |
| 4,243,039 A | 1/1981 | Aginsky |
| 4,273,130 A | 6/1981 | Simpson |
| 4,526,165 A | 7/1985 | Mielnik, Jr. et al. |
| 4,794,656 A | 1/1989 | Henley, Jr. |
| 5,690,672 A | 11/1997 | Cohen |
| 5,993,362 A | 11/1999 | Ghobadi |
| 6,361,548 B1 * | 3/2002 | McEwen ................ 606/201 |
| 6,513,460 B2 | 2/2003 | Fountoulakis |
| 6,537,298 B2 | 3/2003 | Dedo |

(Continued)

FOREIGN PATENT DOCUMENTS

BE    400213    1/1934

(Continued)

OTHER PUBLICATIONS

Office Action dated Mar. 22, 2010, issued in European Patent Application No. 05757785.0.

(Continued)

*Primary Examiner* — Kurt Fernstrom
(74) *Attorney, Agent, or Firm* — Holme Roberts & Owen LLP

(57) ABSTRACT

A training tourniquet for use in training a user or another person, such as a medic, includes a non-functioning tensioning mechanism to model application of developing a tensile force in a strap of a tourniquet. The training tourniquet has particular application to training field personnel, such as medics and soldiers as to how to apply a tourniquet, without actually creating a compressive force that could damage a person's tissue during the training or practice sessions. In one embodiment, an inoperative windlass can be rotated to simulate the action necessary to create tension in a strap of a real tourniquet, however, the inoperative windlass spins around without actually tightening a strap of the training tourniquet.

17 Claims, 9 Drawing Sheets

U.S. PATENT DOCUMENTS

| | | | |
|---|---|---|---|
| 6,540,707 | B1 | 4/2003 | Stark et al. |
| 6,544,188 | B1 | 4/2003 | Morgan et al. |
| 6,602,214 | B2 | 8/2003 | Heinz et al. |
| 6,605,103 | B2 | 8/2003 | Hovanes et al. |
| 6,682,547 | B2 | 1/2004 | McEwen et al. |
| 6,746,470 | B2 | 6/2004 | McEwen et al. |
| 6,796,993 | B2 | 9/2004 | Lambroza |
| 6,884,254 | B2 | 4/2005 | Brooks |
| 6,899,720 | B1 | 5/2005 | McMillan |
| 2001/0041910 | A1 | 11/2001 | McEwen |
| 2002/0016610 | A1 | 2/2002 | Hovanes et al. |
| 2002/0120288 | A1 | 8/2002 | Dedo |
| 2002/0188315 | A1 | 12/2002 | Guzman et al. |
| 2003/0028215 | A1 | 2/2003 | Brooks |
| 2003/0036771 | A1 | 2/2003 | McEwen et al. |
| 2003/0065357 | A1 | 4/2003 | Dedo et al. |
| 2003/0139766 | A1 | 7/2003 | McEwen et al. |
| 2003/0144691 | A1 | 7/2003 | Lambroza |
| 2003/0153936 | A1 | 8/2003 | El-Galley |
| 2003/0167070 | A1 | 9/2003 | McEwen et al. |
| 2003/0236548 | A1 | 12/2003 | Hovanes et al. |
| 2004/0147956 | A1 | 7/2004 | Hovanes et al. |
| 2005/0049630 | A1 | 3/2005 | Ambach |
| 2005/0113866 | A1 | 5/2005 | Heinz et al. |
| 2005/0143689 | A1 | 6/2005 | Ramsey, III |
| 2005/0240217 | A1 | 10/2005 | Jennifer et al. |
| 2005/0273134 | A1 | 12/2005 | Esposito |
| 2008/0221612 | A1 | 9/2008 | Rose |

FOREIGN PATENT DOCUMENTS

| | | |
|---|---|---|
| GB | 2027149 | 2/1980 |

OTHER PUBLICATIONS

Office Action dated Sep. 3, 2009, issued in U.S. Appl. No. 11/846,382.
Office Action dated Apr. 16, 2010, issued in U.S. Appl. No. 11/846,382.
Brill et al. "Bier's Block; 100 Years Old and Still Going Strong!" ACTA Anaesthesiologica Scandinavica, 2004, No. 48, pp. 117-122.
Kam et al "The Arterial Tourniquet: Pathophysiological Consequences and Anaesthetic Implications", Anaesthesia, 2001, No. 56, Blackwell Science Ltd., pp. 534-545.
Klenerman, L. "The Tourniquet Manual—Principles and Practice," 2003, Springer-Verlag London Limited, Chap. 1, pp. 3-11.
McEwen et al. "Tourniquet Safety in Lower Leg Applications", Orthopaedic Nursing, vol. 21, No. 5, Sep./Oct. 2002.
Parsons, Donald L. et al., "Tourniquets—Lifesavers on the Battlefield", article published on www.professionalsoldiers.com dated Oct. 13, 2004.
U.S. Department of Labor et al. "First Aid Book", reprinted 1993, first publication date unknown, pp. 64-66.
Welling et al "A Balanced Approach to Tourniquet Use: Lessons Learned and Relearned", American College of Surgeons, vol. 203, No. 1, Jul. 2006, Elsevier, Inc.
Webpage from www.EBay.com for Non-Pneumatic Tourniquet Olive Drab, marketed by Specialized Equipment, printed Aug. 20, 2009.
Office Action dated Mar. 17, 2009, issued in U.S. Appl. No. 11/147,806.
Response to Office Action dated Aug. 14, 2009, filed in U.S. Appl. No. 11/147,806.
Calkins et al., May 2000, "Evaluation of Possible Battlefield Tourniquet Systems for the For-Forward Setting," Military Medicine, vol. 165(5):379-384.
Crisp; Jul. 18, 2005, "New Tourniquet Issued to Deployed Soldiers"; Defend America New Article; 2 pp.
Holcomb, Jul. 28, 2004, "Tourniquet Recommendations from USAISR"; US Army Institute of Surgical Research; 2 pp.
Webpages for "The Ratchet Tourniquet," Chinook Medical Gear, Inc.; (at least as early as Jan. 20, 2005), 3 pp.
Statement for Information Disclosure Statement by Mark Esposito, signed Oct. 5, 2008 (3 page document).
Statement for Information Disclosure Statement by Mark Esposito, signed Oct. 5, 2008 (2 page document).
U.S. Appl. No. 11/846,382, filed Aug. 28, 2007, by Mark Esposito et al.
International Search Report and Written Opinion, mailed Oct. 3, 2008, for Application No. PCT/US2005/020111.
Supplementary Search Report dated Sep. 28, 2009, issued in European Application No. 05757785.0.
Office Action dated Sep. 16, 2009, issued in Israeli Application No. 179769.

* cited by examiner

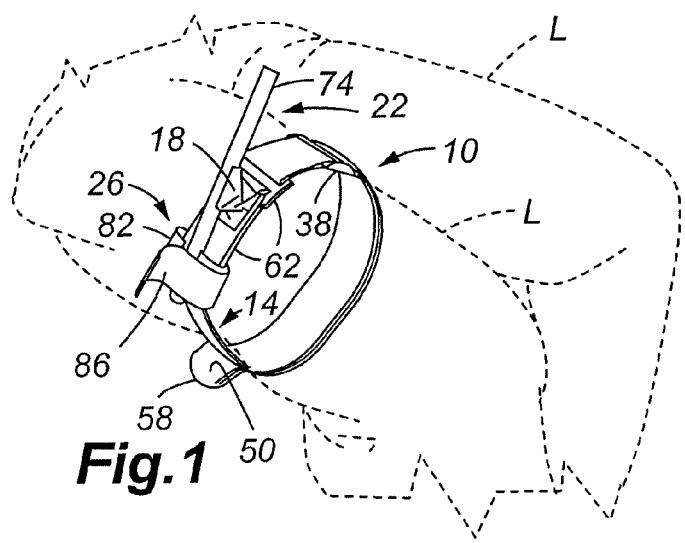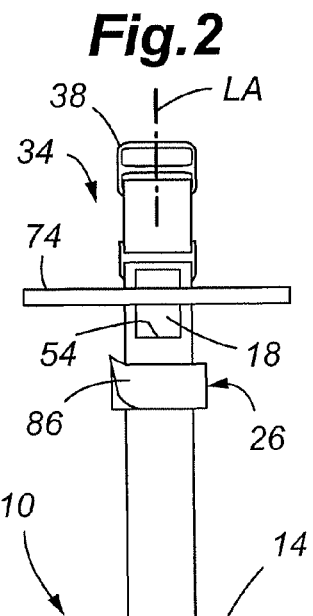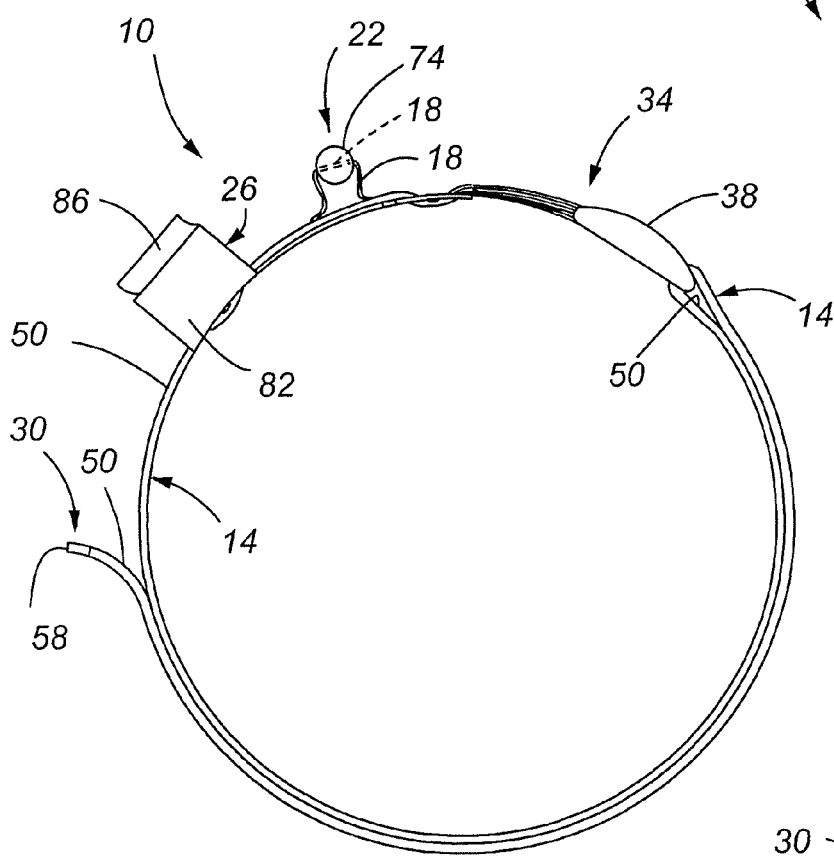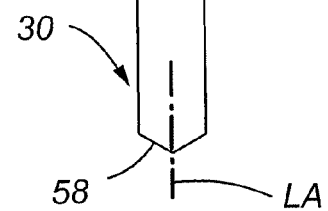

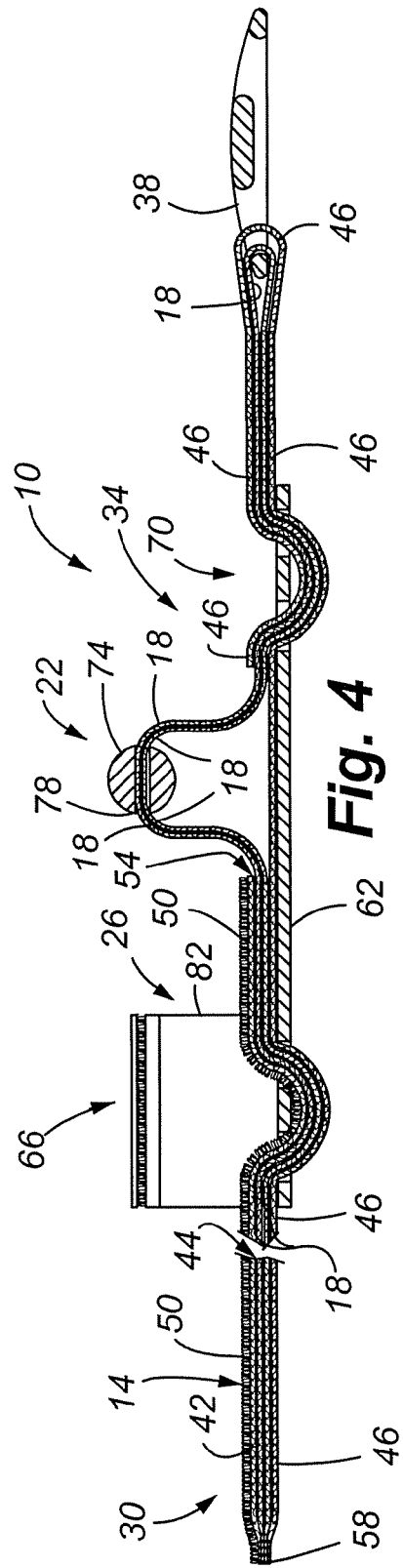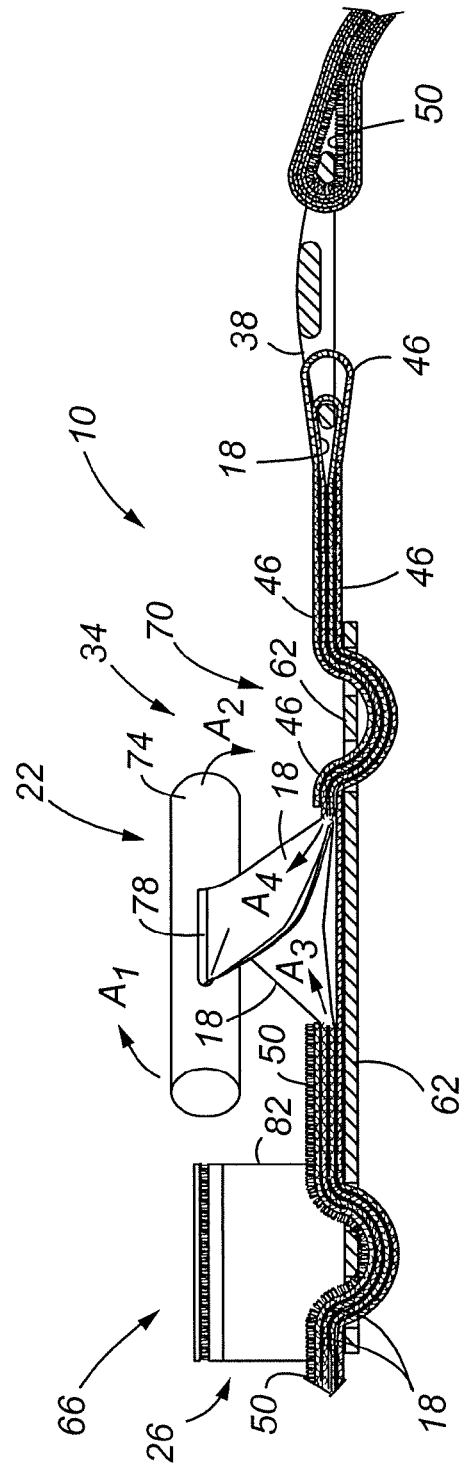

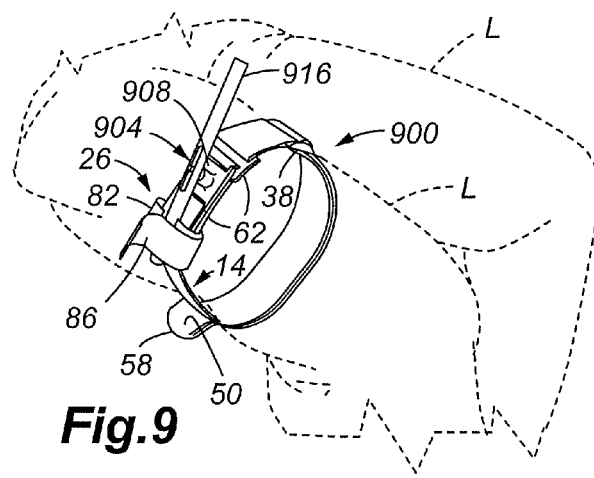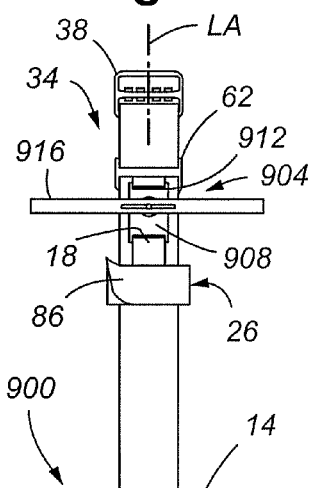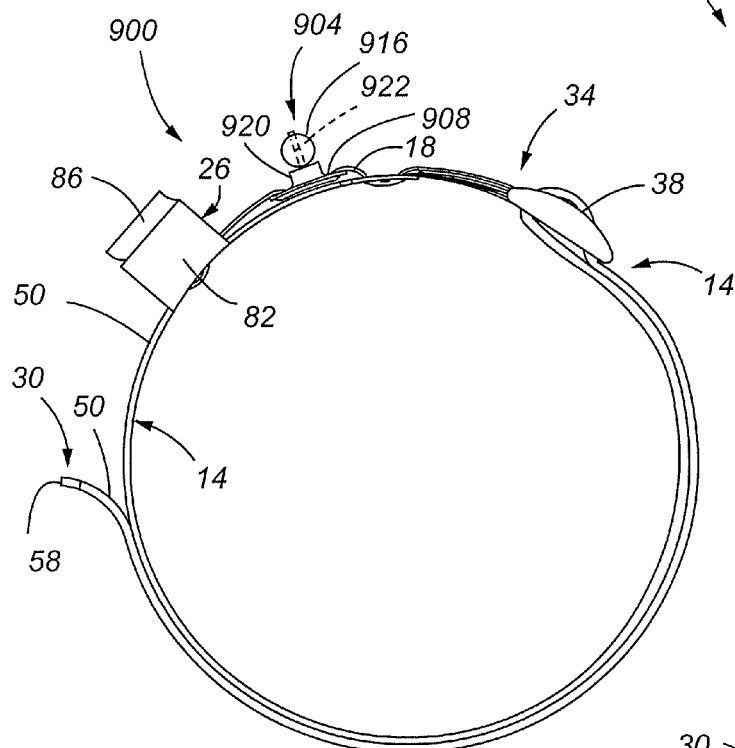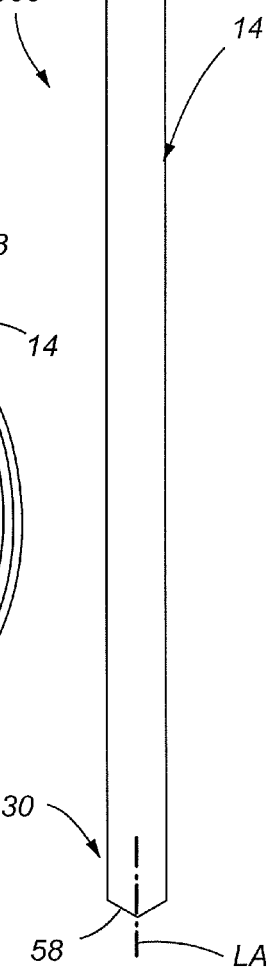
Fig. 9
Fig. 10
Fig. 11

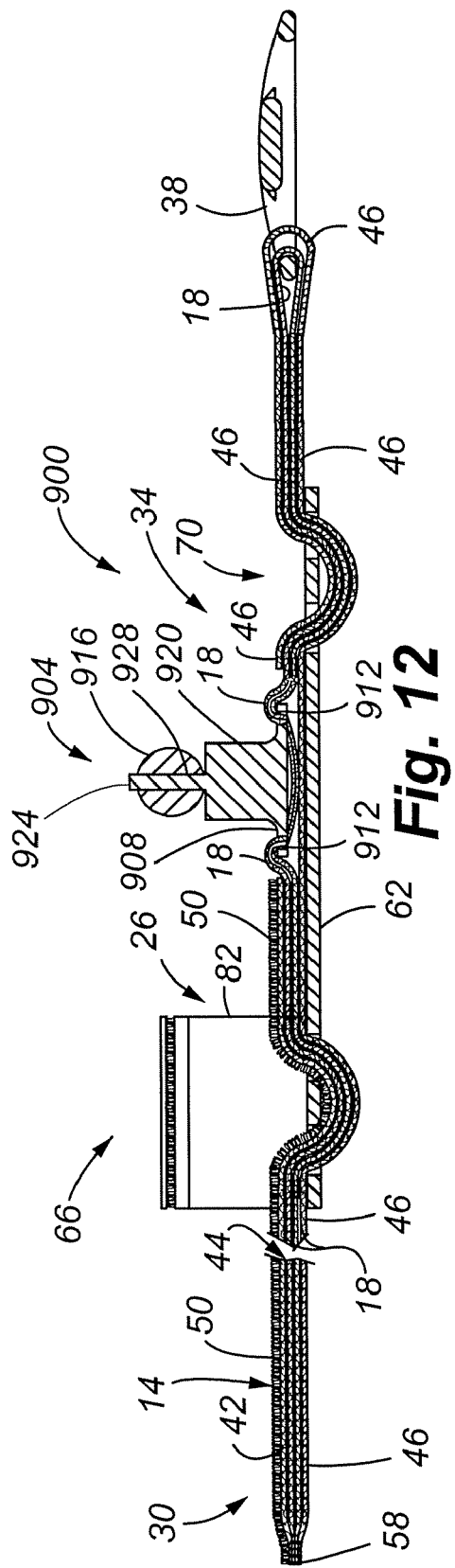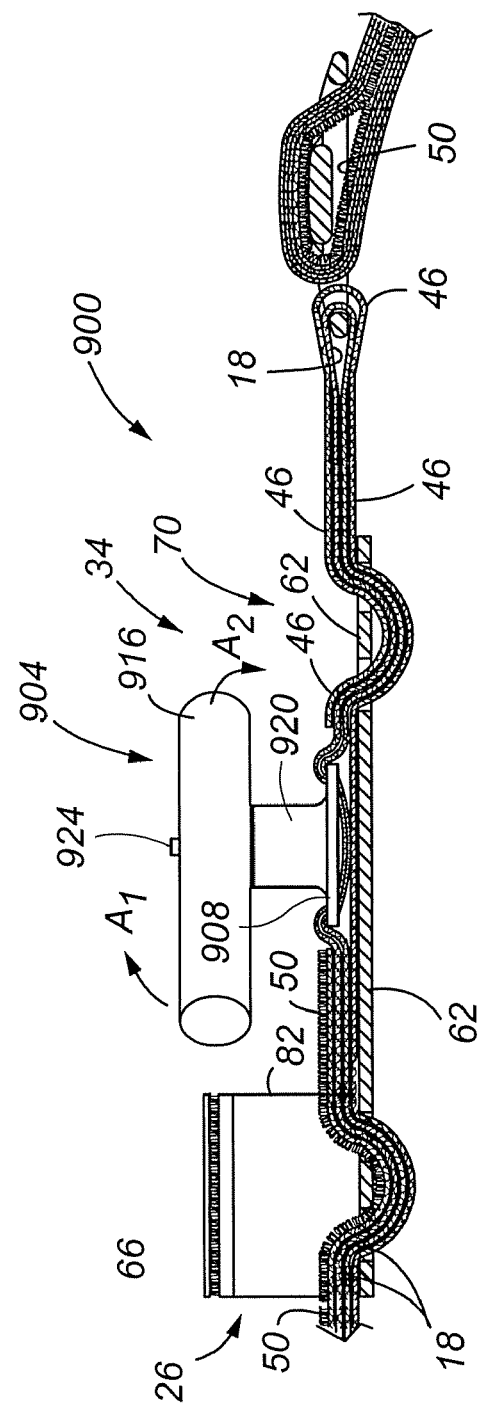

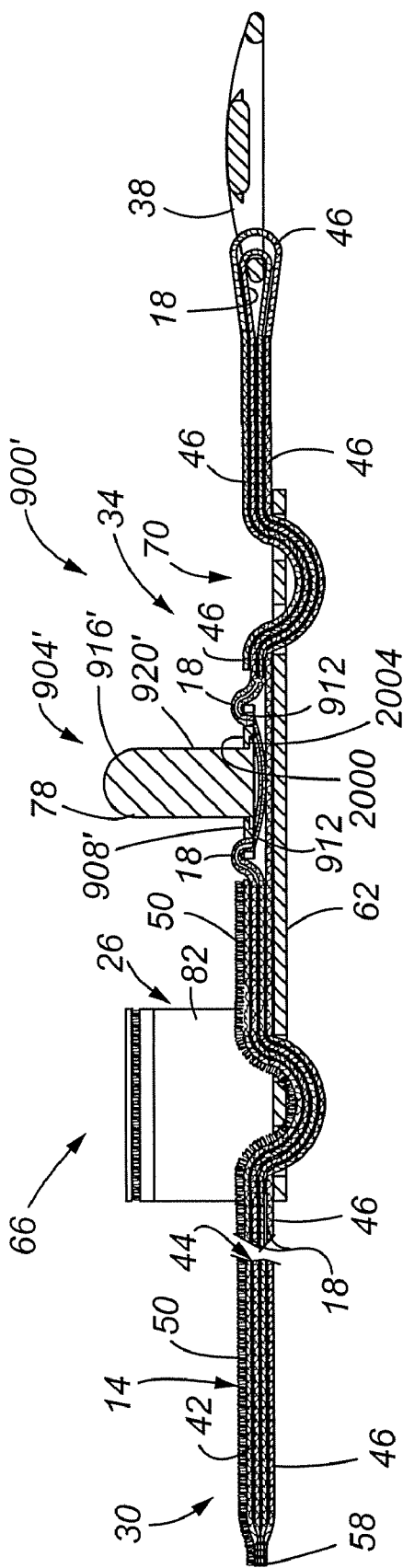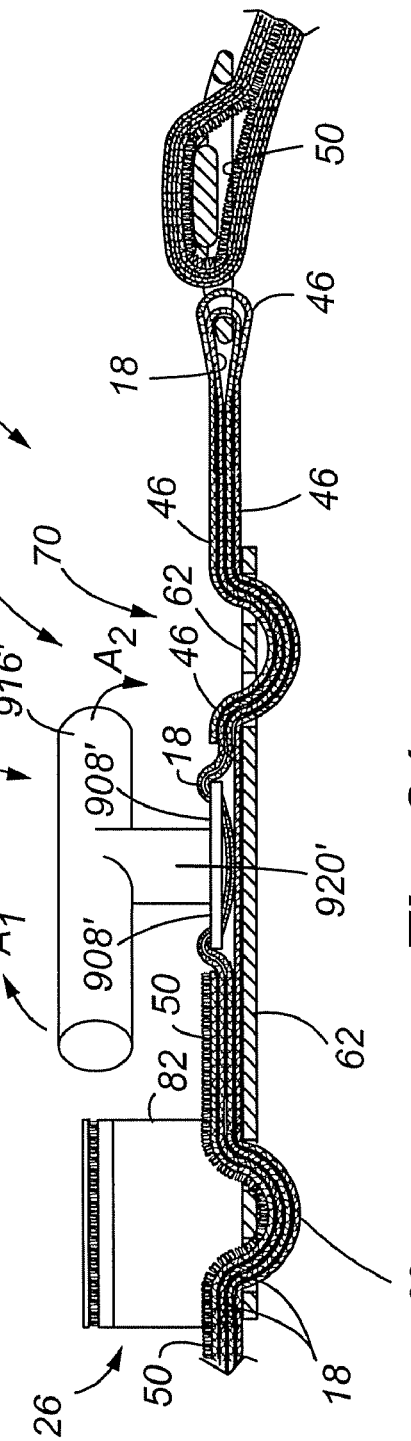

TRAINING TOURNIQUET AND METHOD OF USE

CROSS REFERENCE

The present application claims the benefit of U.S. Provisional Patent Application No. 60/947,337 filed on Jun. 29, 2007 entitled "Training Tourniquet and Method of Use," the entire disclosure of which is incorporated herein by reference in its entirety for all purposes. The present application also cross references, but does not claim priority to U.S. patent application Ser. No. 11/147,806 entitled "Tourniquet and Method of Use" filed on Jun. 6, 2005, the entire disclosure of which is incorporated herein by reference in its entirety for all purposes.

FIELD OF THE INVENTION

The present invention relates to a novel training device, and more particularly, to a novel training tourniquet device for training personnel in the use of restricting the flow of blood.

BACKGROUND

Loss of blood is a major cause of death in emergency situations in which the injured person is alone or medical assistance is not immediately available. The use of a tourniquet to stop blood loss from an injured arm or leg is a well-known technique for preventing death in these situations. In general, for emergency use where the victim is alone, the victim must be able to apply the tourniquet to his or her own arm or leg and occlude blood flow using only one hand. If the victim is not alone, one or more additional people can either apply the tourniquet to the injured person, or at least assist with applying the tourniquet to the injured person. However, whether the injured person is alone or is with someone who can assist in applying the tourniquet, it would be advantageous for at least one of either the injured person or the additional person to understand how to apply the tourniquet.

Tourniquets generally generate inward radial compression forces on a limb by being put into high levels of circumferential tension when wrapped around the limb. A tourniquet used in training could potentially cause injury to a volunteer pretend patient or one's self if the tourniquet is actually applied with some non-trivial amount of pressure. This is because modern tourniquets can generate relatively significant compressive forces to a person's appendage that cause soft tissue damage. More particularly, a real tourniquet includes a way of applying a relatively high amount of pressure around a limb to reliably and predictably stop arterial blood flow. Therefore, if one or more people are practicing or training how to use a tourniquet, and if the tourniquet is an actual functioning tourniquet, and if, as one would reasonably expect, the training includes learning how to apply and tighten the tourniquet, and then actually practicing tightening the tourniquet, then non-trivial amounts of compressive force may be unknowingly and/or inadvertently applied by a trainee. As a result, even in a training situation a modern tourniquet can then cause actual unnecessary injuries to nerves, muscles and the limb. Thus, it would be advantageous to provide a tourniquet that can be repeatedly used in a training situation, while also not actually applying compressive forces that cause injury to the person pretending to be injured or trying to learn how to apply a tourniquet to one of their own appendages.

SUMMARY

These and other needs are addressed by the various embodiments and configurations of the present invention. The present invention comprises a training tourniquet for demonstrating and/or practicing how to use a real tourniquet to restrict the flow of blood in a body part, such as a person's arm or leg. Thus, in accordance with embodiments of the present invention, a training tourniquet is provided, the training tourniquet comprising a first elongated member including a buckle, and a second elongated member slidably connected to the first elongated member. In addition, the training tourniquet comprises a non-functioning tensioning mechanism that is located proximate the second elongated member, wherein the application of a compressive force is not applied to the body part upon modeling the application of a tensile force to the second elongated member using the non-functioning tensioning mechanism, and wherein substantially no compressive force is applied to the body by practicing use of the non-functioning tensioning mechanism.

In accordance with embodiments of the present invention, the non-functioning tensioning mechanism may comprise an inoperative windlass, or non-functioning mechanism, such as a non-functioning ratchet. In addition, for training tourniquets utilizing an inoperative windlass as the non-functioning tensioning mechanism, the training tourniquet may also comprise a securing mechanism interconnected to the first elongated member, wherein the securing mechanism is adapted for securing the inoperative windlass after practicing the application, but not actually applying a tensile force to the second elongated member. In accordance with embodiments of the present invention, the securing mechanism comprises at least one hooked catch, or a securing strap, or at least one hooked catch and a securing strap. When used, the securing strap is preferably interconnected to the outer sleeve and is preferably oriented transversely to a longitudinal axis of the outer sleeve, wherein the securing strap is adapted to secure the inoperative windlass.

The present invention includes a variety of possible configurations. Thus, in accordance with embodiments of the present invention, a training tourniquet for practicing how to restrict a flow of blood in a body part is provided, the training tourniquet comprising a non-functioning means for circumferentially surrounding the body part, a means for modeling compressing the body part, wherein the means for modeling compressing slidably engages the means for circumferentially surrounding. In addition, the tourniquet comprises a means for modeling tensioning the means for modeling compressing, wherein substantially no tensile force is actually applied to the non-functioning means for modeling compressing using the means for modeling tensioning, and wherein substantially no compressive force is applied to the body part.

Various embodiments of the present invention are set forth in the attached figures and in the detailed description of the invention as provided herein and as embodied by the claims. It should be understood, however, that this Summary of the Invention may not contain all of the aspects and embodiments of the present invention, is not meant to be limiting or restrictive in any manner, and that the invention as disclosed herein is and will be understood by those of ordinary skill in the art to encompass obvious improvements and modifications thereto.

Additional advantages of the present invention will become readily apparent from the following discussion, particularly when taken together with the accompanying drawings.

BRIEF DESCRIPTION OF THE DRAWINGS

FIG. 1 is a perspective view of an actual tourniquet applied to a person's right leg (as shown in dashed lines);

FIG. 2 is a plan view of the device shown in FIG. 1, where the device is stretched out along its longitudinal axis;

FIG. 3 is a side elevation view of the device shown in FIG. 1, where the device is shown prior to tightening the device using the windlass;

FIG. 4 is a cross sectional view of the device shown in FIG. 2 with the windlass in an unwound position;

FIG. 5 is the same cross section view of the device as shown in FIG. 4, but with the outer sleeve looped through the buckle and the windlass partially rotated;

FIG. 9 is a perspective view of an embodiment of a training tourniquet applied to a person's right leg (as shown in dashed lines);

FIG. 10 is a plan view of the device shown in FIG. 9, where the device is stretched out along its longitudinal axis;

FIG. 11 is a side elevation view of the device shown in FIG. 9, where the device is shown prior to modeling tightening the device using the inoperative windlass;

FIG. 12 is a cross sectional view of the device shown in FIG. 10 with the inoperative windlass modeling an unwound position;

FIG. 13 is the same cross section view of the device as shown in FIG. 12, but with the outer sleeve looped through the buckle and the inoperative windlass in a partially rotated position;

FIG. 20 is a cross sectional view of the device shown in FIG. 18 with the inoperative windlass modeling an unwound position;

FIG. 21 is the same cross section view of the device as shown in FIG. 20, but with the outer sleeve looped through the buckle and the inoperative windlass in a partially rotated position;

Figure 6:
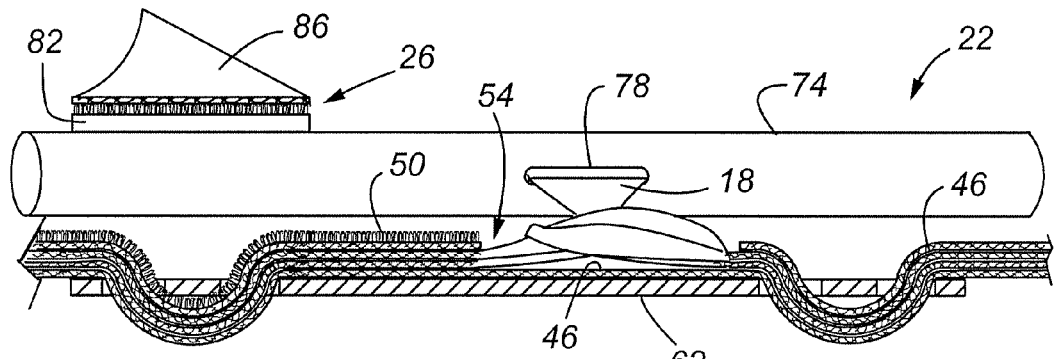
FIG. 6 is a cross sectional view of a portion of the device with the windlass in a wound position.

The drawings are not necessarily to scale, and may, in part, include exaggerated dimensions for clarity.

DETAILED DESCRIPTION

The present invention comprises a training tourniquet that can be used to practice and/or train how to use a real tourniquet. The training tourniquet allows a person to practice how to use a real tourniquet, but with the benefit of not actually applying a compressive force to the appendage via the tensioning mechanism, because in the training tourniquet the tensioning mechanism is actually a non-functioning tension mechanism.

To understand different embodiments of the training tourniquet, real versions of tourniquets are also illustrated and described. Referring now to FIG. 1, an actual functioning or real tourniquet 10 is shown. The real tourniquet 10 comprises a first elongated member or an outer sleeve 14, a second elongated member, inner tightening member or inner strap 18, a tightening mechanism 22 and a securing mechanism 26. As shown in FIG. 1, the real tourniquet 10 can be applied to an appendage, as for example, leg L, and then tightened to restrict the flow of blood to the leg L.

Referring now to FIG. 2, the real tourniquet 10 is shown prior to use, or in a stretched-out orientation. The outer sleeve 14 comprises a longitudinally extensive material having a first end 30 and a second end 34. The second end 34 includes a restraining mechanism comprising a buckle 38. When the real tourniquet 10 is applied to a limb, such as leg L shown in FIG. 1, the first end 30 is looped through the buckle 38 and pulled tight around the appendage, thus providing a means for circumferentially surrounding or encircling the limb. FIG. 3 depicts the real tourniquet 10 after the first end 30 has been looped through the buckle 38.

Referring now to FIG. 4, the outer sleeve 14 may be formed of two panels comprising an upper or first panel 42 and a lower or second panel 46. The edges of the panels 42 and 46 are connected, as for example, by sewing, gluing, stapling, clamping, or heat/ultra-sound (sonic) welding, or combinations thereof. Outer sleeve 14 includes a pocket, interior area or inner space 44 between the panels 42 and 46. The first panel 42 comprises an outer surface 50 that includes hook and loop structures, or both hook structures and loop structures along substantially the entire length of the outer sleeve 14 between the first end 30 and an opening 54 where the inner strap 18 is exposed between the first panel 42 and second panel 46 of the outer sleeve 14. Thus, when the first end 30 of the outer sleeve 14 is looped through the buckle 38, the outer surface 50 may be applied to itself, thereby securing the position of the outer sleeve 14. The first panel 42 may comprise a length of OMNI-TAPE® (Velcro Industries B.V., Amsterdam, Netherlands), wherein the fastening surface comprises both hook and loop structures on the outer surface 50 as depicted in FIG. 4. The use of a combination of both hook and loop structures on the outer surface 50 of the outer sleeve 14 provides the advantage of the tourniquet being quickly adjustable when in use to accommodate a variety of size appendages, as for example, from a person's thigh to a person's forearm.

In use, to size the tourniquet to the appendage, the user simply wraps the tourniquet around the subject appendage, loops the first end 30 of the outer sleeve 14 through the buckle 38, pulls the tourniquet reasonably tight, and then presses the outer surface 50 together detachably interlocking first and second portions of the outer surface 50 together to interlock the hook and loop structures of the outer surface 50 within the region where the outer surface 50 overlaps beyond the buckle 38.

Referring still to FIG. 4, the inner strap 18 is shown between the first panel 42 and the second panel 46 of the outer sleeve 14. The inner strap 18 comprises a length of nylon binding strap (also known as nylon binding tape) that extends from first end 30 of the outer sleeve 14 to the buckle 38 and returns to the first end 30 such that the inner strap 18 comprises a loop. The ends of the inner strap 18 are anchored only at the tip 58 of the first end 30 of outer sleeve 14, as for example, by sewing, gluing, stapling, clamping, or heat/ultrasound (sonic) welding, or combinations thereof. Thus, the inner strap 18 can slide within the interior space 44 of the outer sleeve 14. Accordingly, the inner strap 18 comprises a material that has frictional characteristics allowing it to slide within the interior space 44 of the outer sleeve 14 when a tensile force is applied to the inner strap 18.

The real tourniquet 10 may be configured such that a single layer (i.e., not a loop) of material is used to form the inner strap 18. Here, a first end of the inner strap 18 is anchored at or near the tip 58 of the first end 30 of the outer sleeve 14, and a second end of the inner strap 18 is anchored at or near the buckle 38, with the middle portion not anchored to the outer sleeve 14, and thereby able to slide within the outer sleeve 14. The tensioning mechanism 22 can be used to tighten the inner strap 18, such as by winding the windlass 74 to develop a tension force in the inner strap 18.

Referring still to FIG. 4, the real tourniquet 10 includes a base member 62. A first end 66 of base member 62 includes a securing mechanism 26, as will be discussed below. The second panel 46 of the outer sleeve 14 extends over at least a portion of the base member 62, passes through a means for looping, such as buckle 38, and folds back to a second end 70 of the base member 62. The inner strap 18 emerges from the outer sleeve 14 at opening 54 where it is connected to the tightening mechanism 22. The tightening mechanism 22 comprises a windlass 74 that is shown in an unwound position. The inner strap 18 passes through a slot or aperture 78 in the windlass 74, and as described above, the inner strap 18 extends to and around the buckle 38.

Figure 7:
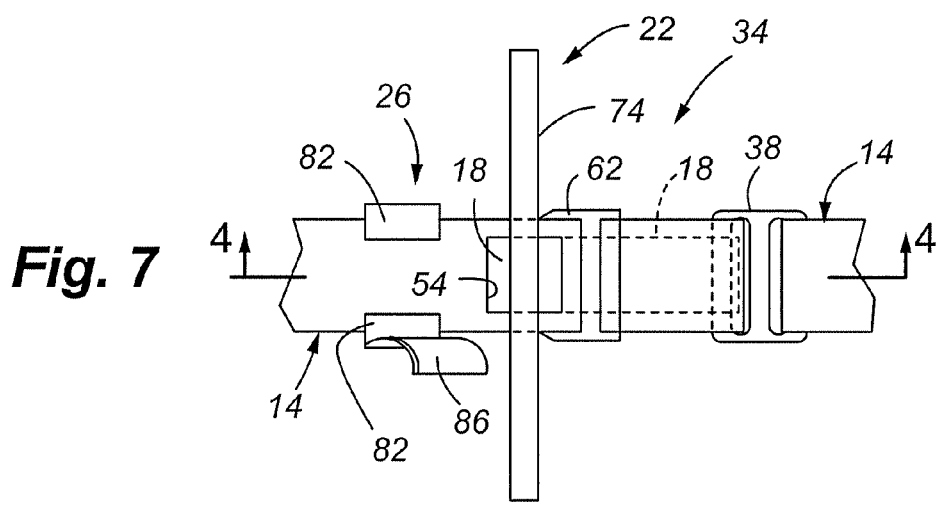
FIG. 7 is a plan view of the buckle end of the device with the outer sleeve looped through the buckle and the windlass in an unwound position.

Referring to FIG. 7, a plan view of the second end 34 of the outer sleeve 14 is shown. Here, the outer sleeve 14 has been looped through buckle 38; however, the tension mechanism 22, comprising a windlass 74, as will be described below, has not been wound to tighten the inner strap 18.

Figure 8:
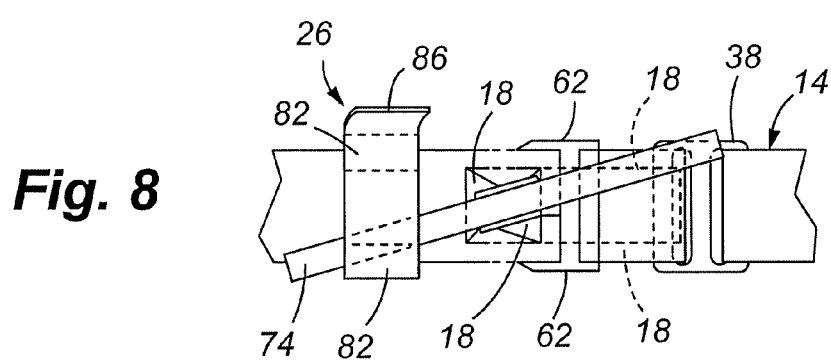
FIG. 8 is a plan view of the buckle end of the device with the outer sleeve looped through the buckle and the windlass in a wound position.
Figure 14:
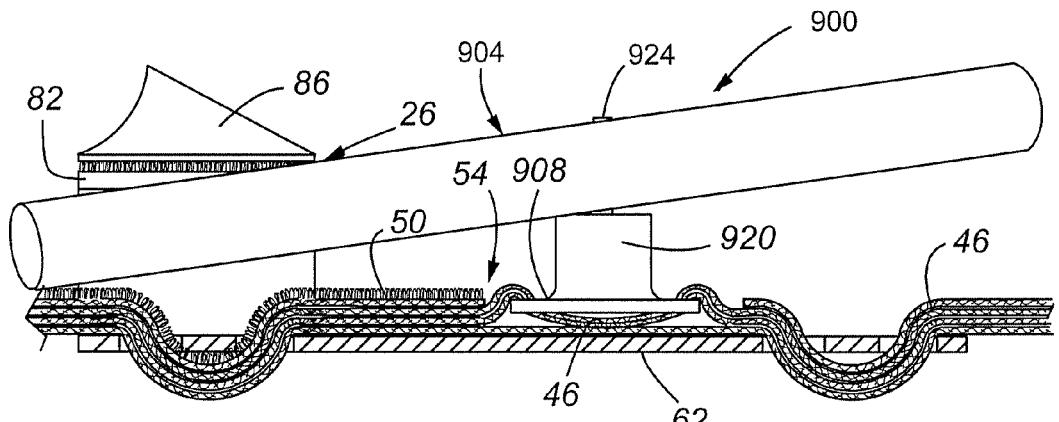
FIG. 14 is a cross sectional view of a portion of the device of FIG. 9 with the inoperative windlass modeling a wound position.
Figure 15:
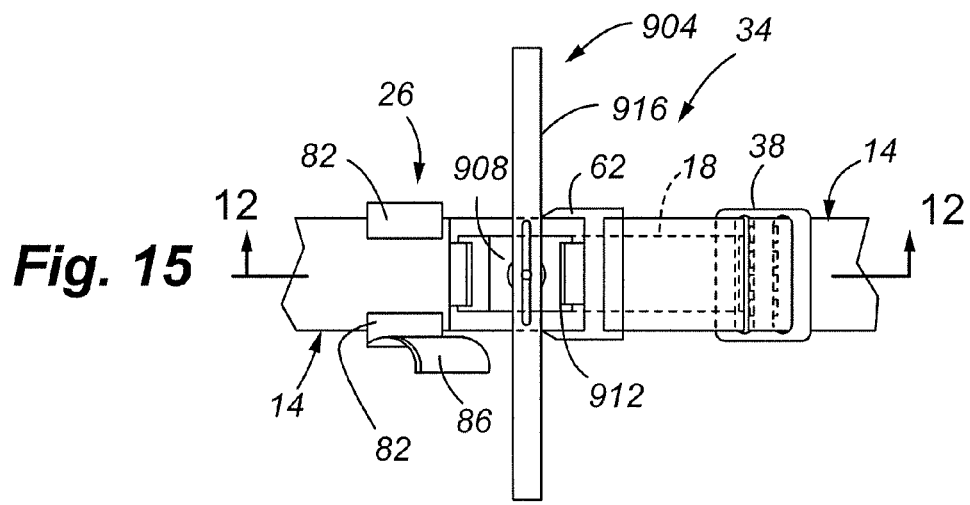
FIG. 15 is a plan view of the buckle end of the device if FIG. 9 with the outer sleeve looped through the buckle and the inoperative windlass modeling an unwound position.
Figure 16:
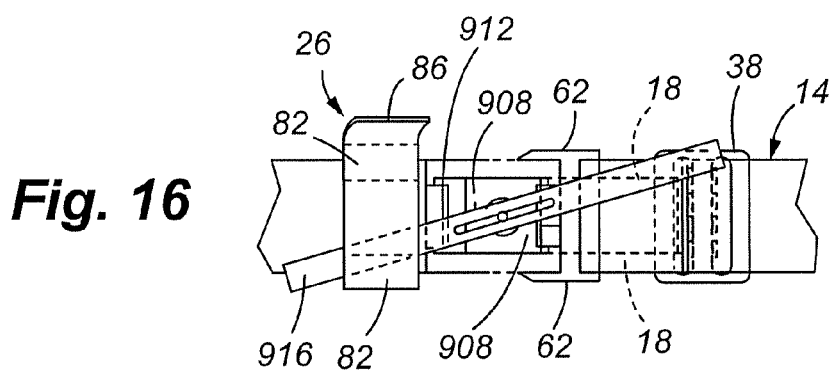
FIG. 16 is a plan view of the buckle end of the device with the outer sleeve looped through the buckle and the inoperative windlass modeling a wound position.
Figure 17:
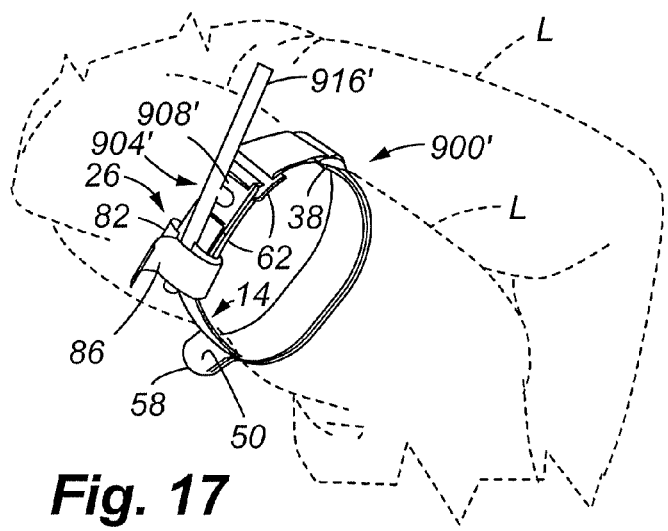
FIG. 17 is a perspective view of a different version of a training tourniquet, wherein the training tourniquet is applied to a person's right leg (as shown in dashed lines)
Figure 18:
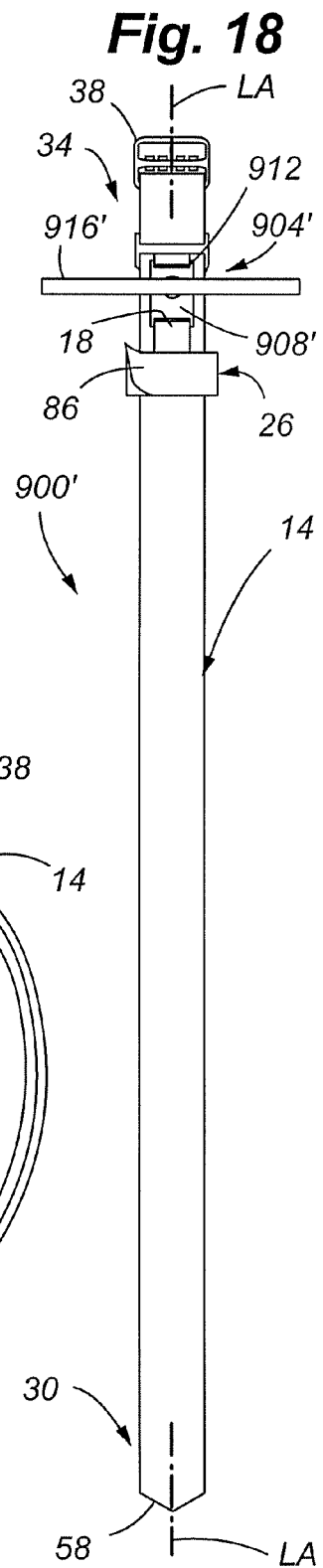
FIG. 18 is a plan view of the device shown in FIG. 17, where the device is stretched out along its longitudinal axis.
Figure 19:
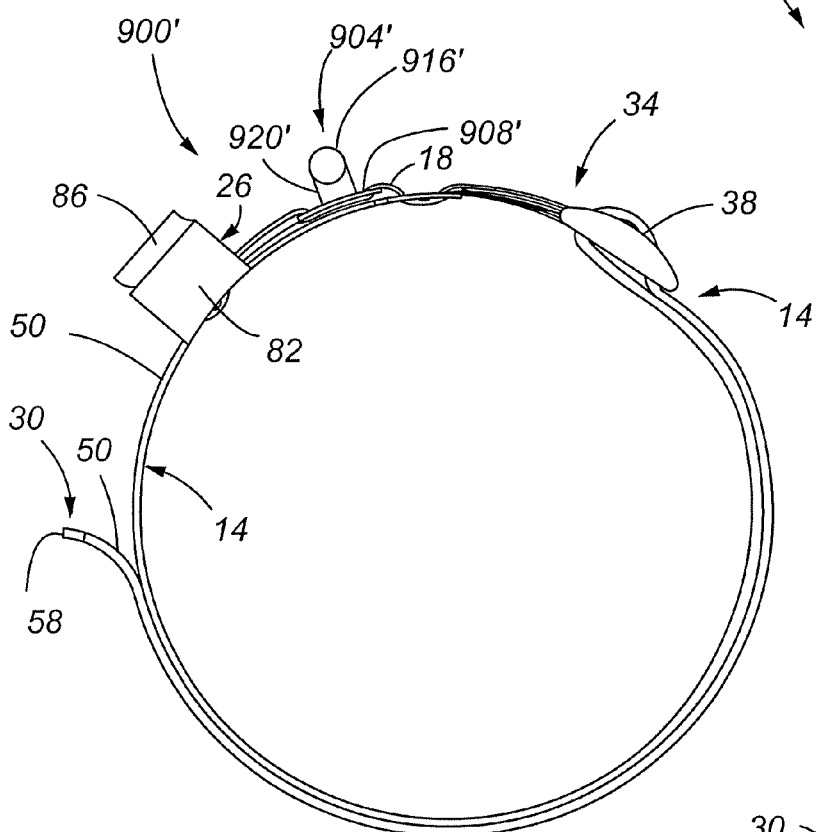
FIG. 19 is a side elevation view of the device shown in FIG. 17, where the device is shown prior to modeling tightening the device using the inoperative windlass.
Figure 22:
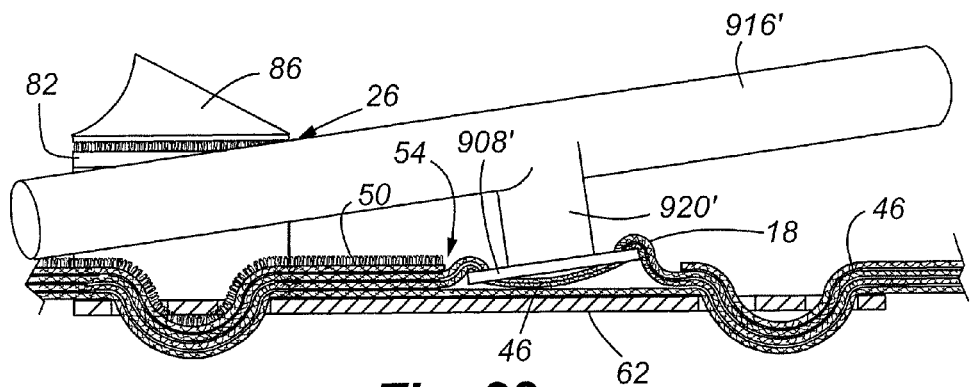
FIG. 22 is a cross sectional view of a portion of the device of FIG. 17 with the inoperative windlass modeling a wound position.
Figure 23:
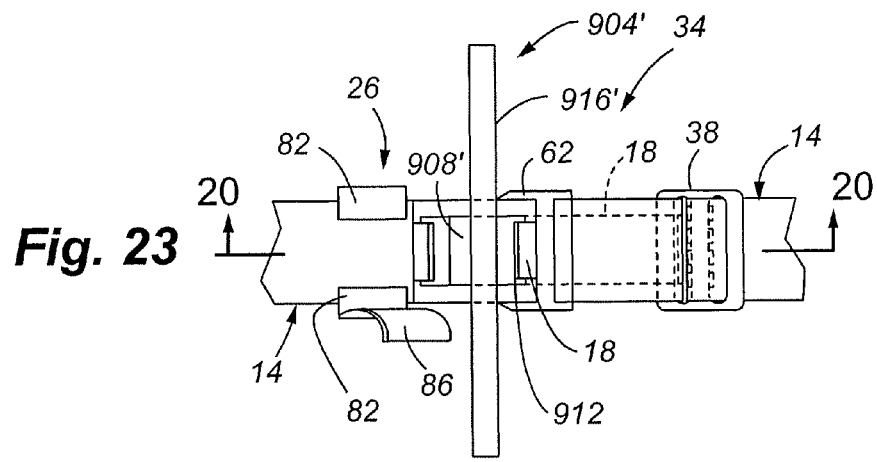
FIG. 23 is a plan view of the buckle end of the device if FIG. 17 with the outer sleeve looped through the buckle and the inoperative windlass modeling an unwound position.
Figure 24:
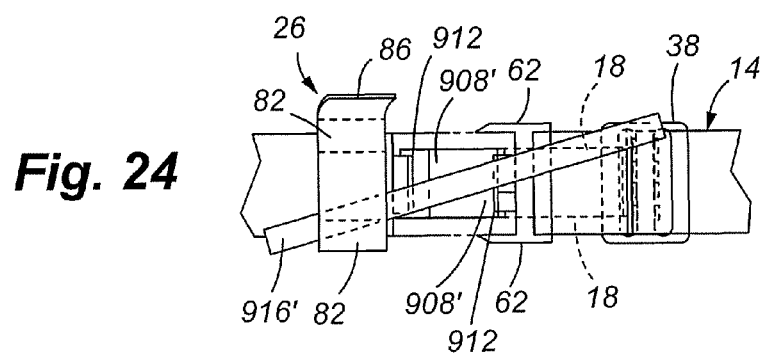
FIG. 24 is a plan view of the buckle end of the device with the outer sleeve looped through the buckle and the inoperative windlass modeling a wound position.

Referring now to FIG. 8, a plan view of the second end 34 of the outer sleeve is shown. Here, the outer sleeve 14 has been looped through buckle 38 and the windlass 74 has been partially wound, thereby applying a tensile force to the inner strap 18. Since the end of the inner strap 18 is secured to the tip 58 of the outer sleeve 14, when the windlass 74 is rotated, the inner strap 18 slides within the outer sleeve 14, essentially scrunching the outer sleeve 14 relative to the inner strap 18 as the inner strap 18 is increasingly tightened. The tightened inner strap 18 provides a substantially even radial compressive pressure to the limb to which the real tourniquet 10 is being applied.

Referring now to FIG. 5, a cross sectional view of the real tourniquet 10 is shown, including the second end 34 of real tourniquet 10 with the windlass 74 in a partially wound position. More particularly, in use, after the first end 30 of the outer sleeve 14 is passed through the buckle 38 and secured around an appendage or limb, such as leg L shown in FIG. 1, the windlass 74 is rotated, such as in the direction of arrows A1 and A2, to apply a tensile force to at least a portion of the inner strap 18. Since the inner strap 18 is secured to the tip 58 of first end 30 of the outer sleeve 14, the inner strap 18 slides in the direction of arrows A3 and A4 within the outer sleeve 14 as the windlass 74 is rotated, thereby pulling the inner strap and providing a circumferentially applied compression force to the appendage. After the windlass 74 is tightened, the tourniquet restricts the blood flow in the appendage.

Referring now to FIG. 6, a cross sectional view of the second end 34 of real tourniquet 10 is shown with the windlass 74 in a wound position. After the windlass 74 has been sufficiently tightened to restrict the arterial blood flow in the appendage, the windlass 74 may be secured using securing mechanism 26. The securing mechanism 26 provides a means for securing or preventing the windlass 74 from unwinding. Thus, the securing mechanism 26 maintains the wound position of the windlass 74, and thereby maintains the tension in the inner strap 18.

As best seen in FIGS. 1, 7, and 8, the securing mechanism 26 comprises a pair of opposing hooked catches 82 set substantially transverse to the longitudinal axis LA-LA of the real tourniquet 10. More particularly, the hooked catches 82 are sized to cup or hold the windlass, or a portion thereof, and prevent it from unwinding. Two opposing catches 82 allows the user to rotate the windlass 74 in either direction, with one of the two catches 82 always able to prevent the windlass 74 from unwinding. The securing mechanism 26 may comprise a securing strap positioned transversely to a longitudinal axis LA-LA of the outer sleeve 14. As for example, a transversely oriented strap having hook and loop fastening portions, or an elastic band engaging a hook or button may be provided to secure the windlass 74 in its wound position.

A transversely oriented strap 86 may be used in combination with the hooked catches 82. Such a combination of structures allows the user to secure the windlass 74 and move about (or be moved by another person) with less concern of the windlass 74 dislodging from the hooked catches 82 and unwinding. The outer surface of the hooked catches may comprise a hook or loop material, and a surface of the strap 86 may comprise a complementary hook or loop material to interlock with the material on the hooked catches 82.

Referring now to FIGS. 9-16, and in accordance with an embodiment of the present invention, a training tourniquet 900 is shown that includes a number of structures of real tourniquet 10; however, training tourniquet 900 features a non-functioning tension mechanism 904. The non-functioning tension mechanism 904 includes a base portion 908 that is interconnected to another portion of the training tourniquet 900, such as the base member 62 or the inner strap 18. For the embodiment of the training tourniquet 900 shown in FIGS. 9-16, the base portion 908 includes apertures 912 and inner strap 18 passes through apertures 912. Alternatively, the base portion 908 may be stapled, glued, welded, or otherwise affixed to the inner strap 18. An inoperative windlass 916 is interconnected to the base portion 908, such as by a stem 920. As used herein, the term "inoperative windlass" means a windlass that does not tighten a strap of the training tourniquet 900. The inoperable windlass may be rotatable or not. Even in embodiments in which it is rotatable, however, it does not tighten a strap of the trainer tourniquet. Thus, for the embodiment shown in FIGS. 9-16, the inoperative windlass 916 can rotate to simulate tightening of the inner strap 18, however, the rotational action of the inoperative windlass 916 does not actually tighten the inner strap 18. More particularly, the stem 920 either rotates and/or allows rotation of the inoperative windlass 916 such that the inoperative windlass 916 essentially spins without winding the inner strap 18. In one embodiment, and as shown in FIGS. 9-16, the stem 920 includes a shaft 924 that extends into a bore 928 within the inoperative windlass 916, and when the inoperative windlass 916 is rotated, the stem 920 is substantially stationary and the inoperative windlass 916 spins around the shaft 924. Thus, the base portion 908 allows the inoperative windlass 916 to rotate and not transfer any tension to the training tourniquet 900. As shown in FIGS. 9, 10, 15, and 16, the bore 928 may reside within a slot or aperture 78 of the windlass 916, where the slot or aperture is present to reflect where the inner strap 18 may reside, at least for some versions of a working tourniquet, such as real tourniquet 10.

Referring now to FIGS. 17-24, a separate embodiment of a training tourniquet is illustrated that is a modification of the training tourniquet 900. Similar to training tourniquet 900, training tourniquet 900' includes a non-functioning tensioning mechanism 904'. The non-functioning tensioning mechanism 904' includes an inoperative windlass 916' that is fixedly attached to stem 920' such that the inoperative windlass 916' and the stem 920' rotate together. More particularly, base portion 908' includes structure for allowing the stem 920' and the inoperative windlass 916' to rotate together. In one embodiment of the invention, the bottom of stem 920' extends into base portion 908', where the base portion 908' includes a flange 2000 for rotatably holding the flared bottom 2004 of stem 920'. The stem 920' is thus rotatable within the bottom portion 908'.

In summary, training tourniquets 900 and 900' illustrate different ways of allowing the inoperative windlass 916 and 916' to rotate to allow a trainee to model how to apply a tensile force to the inner strap 18, while not actually applying a tensile force to the inner strap 18, thereby avoiding the application of a compressive force to an appendage as a result of practicing the operation of the non-functioning tensioning mechanism 904 and 904'.

In another embodiment of the invention (not shown), a trainer tourniquet comprises an inoperative windlass that is operatively associated with a deformable elastomeric member (not shown) or similar material that allows the rotation of the inoperative windlass without applying a tension to the inner strap. More particularly, the deformable elastomeric member may comprise a plastic or synthetic material, such as a relatively soft plastic, that extends between the windlass and the base portion of the windlass so that the trainee can rotate the inoperative windlass without applying a tension to the inner strap.

In still another embodiment of the invention (not shown), the inner strap is provided with an excessive length of material such that it can be wound, but wherein it is too long to allow the strap to be tensioned by rotating the windlass. Here, the inner strap may pass through the windlass, but because of its length, the windlass is unable to gather the inner strap to provide a tensile force that causes compression of an appendage when used to practice use of the trainer tourniquet.

In still another embodiment of the invention (not shown), the inner strap comprises a stretchable material that is deformable and can be wound by the windlass, but that develops an ineffective amount of tension so that the trainer tourniquet does not effectively apply a significant compressive force sufficient to occlude blood flow to an appendage during a practice use of the trainer tourniquet.

In still yet another embodiment of the invention (not shown), the stem of the non-functioning tensioning mechanism comprises a safety clutch or slip device. For this embodiment, the strap may also pass through the windlass to more closely model the actual working tourniquet, however, once a relatively small amount of tension is developed in the inner strap, the safety clutch then effectively prevents additional tension from being applied to the inner strap. That is, the safety clutch can be set to limit the amount of tension that can be applied to the inner strap, such that the windlass can rotate and can also apply a tensile force to the inner strap, but wherein the tensile force is limited such that tissue damage cannot occur when practicing or training with the subject training tourniquet.

The above-described alternatives are encompassed by the scope of the present invention.

In accordance with one or more embodiments of the present invention, the training tourniquet may include a safety mechanism, such as a breakaway strap component. In one embodiment of the invention, the inner strap includes a weakened portion such that if a modest tensile force is applied to the inner strap, such as by reconfiguring the non-functioning tensioning mechanism, then the strap breaks so that no damaging compressive forces can be applied to an appendage.

In accordance with embodiments of the present invention, training tourniquets described herein may comprise visual indicator that the device is a training tourniquet and not an actual tourniquet for applying a compressive force to an appendage. In at least one embodiment of the invention, one or more components of the training tourniquet are the color blue. In one or more embodiments of the present invention, the training tourniquet comprises indicia such as "TRAINING DEVICE," "TRAINING TOURNIQUET," "INOPERATIVE," "FOR TRAINING ONLY," "WARNING: NON-OPERATIVE," "DO NOT WIND STRAPS," and the like, including combinations of the foregoing, and further optionally including one or more components of the training tourniquet that are blue in color.

Non-windlass-types of tourniquets are used, and one such device uses a ratchet as the tensioning mechanism. In accordance with at least one embodiment of the present invention, a training tourniquet comprises an inoperative ratchet (not shown) that can be manipulated by will not apply a tensile force to the inner strap.

Embodiments of the one or more present inventions are also directed to methods of using a training tourniquet. In at least one embodiment, a method for training a person how to restrict a flow of blood to a body part is provided, the method comprising:

(a) wrapping a first elongated member around the body part and looping a first portion of the first elongated member through a buckle connected to the first elongated member;

(b) detachably attaching the first portion of the elongated member to a second portion of the elongated member;

(c) operating a non-functioning tensioning mechanism connected to a second elongated member slidably positioned relative to the first elongated member, wherein the non-functioning tensioning mechanism models and does not develop a tensile force in the second elongated member, wherein substantially no compressive force is applied to the body part restricting the flow of blood in the body part by operating the non-functioning tensioning mechanism. The method may further comprise securing the tensioning mechanism using at least one of a hooked catch and a securing strap.

Embodiments of the one or more present inventions also allow a person, such as a soldier, to practice using a tourniquet without actually applying restrictive force to one of their appendages. Accordingly, in at least one embodiment, a method of practicing how to restrict a flow of blood to a body part is provided, the method comprising:

(a) placing a first elongated member for contacting the body part around the body part, and positioning at least a portion of the first elongated member through a restraining mechanism connected to the first elongated member; and (b) operating a non-functioning tensioning mechanism for modeling the application of a tensile force to a second elongated member, the second elongated member not contacting the body part, the second elongated member adapted for slidably engaging the first elongated member, wherein the non-functioning tensioning mechanism does not induce a tensile force in any portion of the second elongated member, wherein substantially no compressive force is applied to the body part restricting the flow of blood in the body part when operating the non-functioning tensioning mechanism. The method may further comprise securing the non-functioning tensioning mechanism using at least one of a hooked catch and a securing strap.

The present invention has application for use in training emergency medical personnel. In addition, the invention also has application for use in veterinary medicine to practice the application of a tourniquet to a body part or limb of an animal.

The present invention, in various embodiments, includes components, methods, processes, systems and/or apparatus substantially as depicted and described herein, including various embodiments, subcombinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance, achieving ease and\or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover though the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A training tourniquet for practicing restricting a flow of blood in a body part, the training tourniquet comprising:
    (a) a first elongated member including a buckle;
    (b) a second elongated member slidably connected to the first elongated member;
    (c) a non-functioning tensioning mechanism connected to at least one of the first and second elongated members;
    wherein substantially no compressive force is applied to the body part upon operating the non-functioning tensioning mechanism.

2. The training tourniquet as claimed in claim 1, wherein the non-functioning tensioning mechanism comprises an inoperative windlass.

3. The training tourniquet as claimed in claim 2, further comprising a securing mechanism interconnected to the first elongated member, wherein the securing mechanism is adapted for securing the non-functioning tensioning mechanism after practicing the application of a tensile force to the second elongated member.

4. The training tourniquet as claimed in claim 3, wherein the securing mechanism comprises at least one hooked catch.

5. The training tourniquet as claimed in claim 3, wherein the securing mechanism comprises a securing strap oriented transversely to a longitudinal axis of the first elongated member.

6. The training tourniquet as claimed in claim 1, wherein the non-functioning tensioning mechanism comprises an inoperative ratchet.

7. The training tourniquet as claimed in claim 1, wherein the second elongated member forms a loop running from a first end of the first elongated member to the buckle and back to the first end of the first elongated member.

8. A training tourniquet for training how to restrict a flow of blood in a body part without restricting the flow of blood in a body, the training tourniquet comprising:
    (a) means for circumferentially surrounding the body part;
    (b) means for modeling compressing the body part, the means for modeling compressing slidably engaging the means for circumferentially surrounding;
    (c) means for modeling tensioning the means for modeling compressing;
    wherein use of the means for modeling tensioning does not apply a tensile force to the means for modeling compressing, and wherein substantially no compressive force is applied to the body part to restrict the flow of blood in the body part using the means for modeling tensioning.

9. The training tourniquet as claimed in claim 8, further comprising means for securing the means for modeling tensioning.

10. The training tourniquet as claimed in claim 8, wherein the means for circumferentially surrounding comprises a means for looping the means for circumferentially surrounding around the body part.

11. The training tourniquet as claimed in claim 8, wherein the means for circumferentially surrounding comprises a means for fastening a portion of a first surface of the means for circumferentially surrounding to a second portion of the first surface of the means for circumferentially surrounding.

12. A training tourniquet for restricting a flow of blood in a body part, the tourniquet comprising:
    (a) an outer sleeve;
    (b) an inner strap in slidable engagement with the outer sleeve; and
    (c) an inoperative windlass connected to the inner strap;
    wherein substantially no compressive force is applied to the body part upon rotating the inoperative windlass.

13. The training tourniquet as claimed in claim 12, further comprising at least one hooked catch interconnected to the outer sleeve, wherein the hooked catch is adapted to secure the inoperative windlass.

14. The training tourniquet as claimed in claim 12, further comprising a securing strap interconnected to the outer sleeve and oriented transversely to a longitudinal axis of the outer sleeve, wherein the securing strap is adapted to secure the inoperative windlass.

15. The training tourniquet as claimed in claim 12, wherein the outer sleeve comprises an upper panel connected to a lower panel, wherein at least a portion of the upper panel comprises hook and loop fasteners.

16. The training tourniquet as claimed in claim 15, wherein the hook and loop fasteners comprises a single component hook and loop fastener having hook and loop on a common surface.

17. A training tourniquet for training how to restrict a flow of blood in a body part, the training tourniquet comprising:
(a) a first elongated member comprising:
  (i) a surface comprising both hook and loop structures;
  (ii) a first end for looping through a second end comprising a buckle;
  (iii) a pocket;
(b) a second elongated member positioned in the pocket, wherein a portion of the second elongated member is connected to the first end of the first elongated member;
(c) an inoperative windlass proximate the second elongated member, wherein the inoperative windlass is rotated to model application of a tensile force in the second elongated member, wherein substantially no compressive force is applied to the body part restricting the flow of blood in the body part upon rotation of the inoperative windlass; and
(d) at least one hooked catch or a securing strap interconnected to the first elongated member for engaging a portion of the inoperative windlass.

* * * * *